United States Patent [19]

Brossoit

[11] Patent Number: 5,230,622
[45] Date of Patent: Jul. 27, 1993

[54] ARTICULATED MIRROR ATTACHMENT FOR DENTAL SUCTION TIPS

[76] Inventor: A. Douglas Brossoit, N. 5908 Belt, Spokane, Wash. 99205

[21] Appl. No.: 929,894

[22] Filed: Aug. 11, 1992

[51] Int. Cl.$^5$ .......................... A61C 1/00; A61C 3/00; A61C 17/06; A61C 17/14
[52] U.S. Cl. .......................................... 433/31; 433/30; 433/91
[58] Field of Search ............... 432/30, 31, 91; 128/21, 128/22

[56] References Cited

U.S. PATENT DOCUMENTS

| | | |
|---|---|---|
| 159,836 | 2/1875 | Osborn .................... 433/30 |
| 838,648 | 12/1906 | Robertson ................ 433/91 |
| 1,079,414 | 11/1913 | Jirka ........................ 433/30 |
| 1,397,090 | 11/1921 | Dimas ...................... 433/30 |
| 1,500,798 | 7/1924 | Campodonico .......... 433/31 |
| 1,509,041 | 9/1924 | Hyams ..................... 128/22 |
| 1,905,633 | 4/1933 | Feltham ................ 433/30 X |
| 2,393,319 | 1/1946 | Freedman ............. 433/91 X |
| 2,436,040 | 2/1948 | Friedman .............. 433/91 X |
| 2,861,342 | 11/1958 | Katz ...................... 433/91 X |
| 2,862,299 | 12/1958 | Reiter ................... 433/91 X |
| 3,777,756 | 12/1973 | Lohr ..................... 433/91 X |
| 3,928,916 | 12/1975 | Hansson ............... 433/91 X |
| 4,354,835 | 10/1982 | Lewis ..................... 433/30 |
| 4,521,185 | 6/1985 | Cohen ..................... 433/31 |

FOREIGN PATENT DOCUMENTS

| | | |
|---|---|---|
| 836701 | 4/1952 | Fed. Rep. of Germany ........ 433/30 |
| 446545 | 12/1947 | Italy ..................................... 433/31 |

Primary Examiner—Gene Mancene
Assistant Examiner—Nicholas D. Lucchesi
Attorney, Agent, or Firm—Wells, St. John, Roberts, Gregory & Matkin

[57] ABSTRACT

An attachment is provided for releasably and adjustably mounting a mirror to a dental suction tip. The attachment includes a collar that will spring clip to the suction tip along the length dimension thereof and will permit both axial and rotational positioning of the attachment on the suction tip. A stud shaft extends from the collar to a first ball joint at one end of an extension arm. The other end of the extension arm includes a second ball joint which is connected to a mirror by a short stub shaft. The stub shaft is mounted to a marginal edge portion of a mirror backing which is crimped over the peripheral edge of the mirror plate. The mirror can be selectively positioned about the pivot points of the ball joints and suction tip to selectively orient the mirror in relation to the suction tip, and to afford a holder, a reflected view of a desired area within a dental patient's mouth.

14 Claims, 3 Drawing Sheets

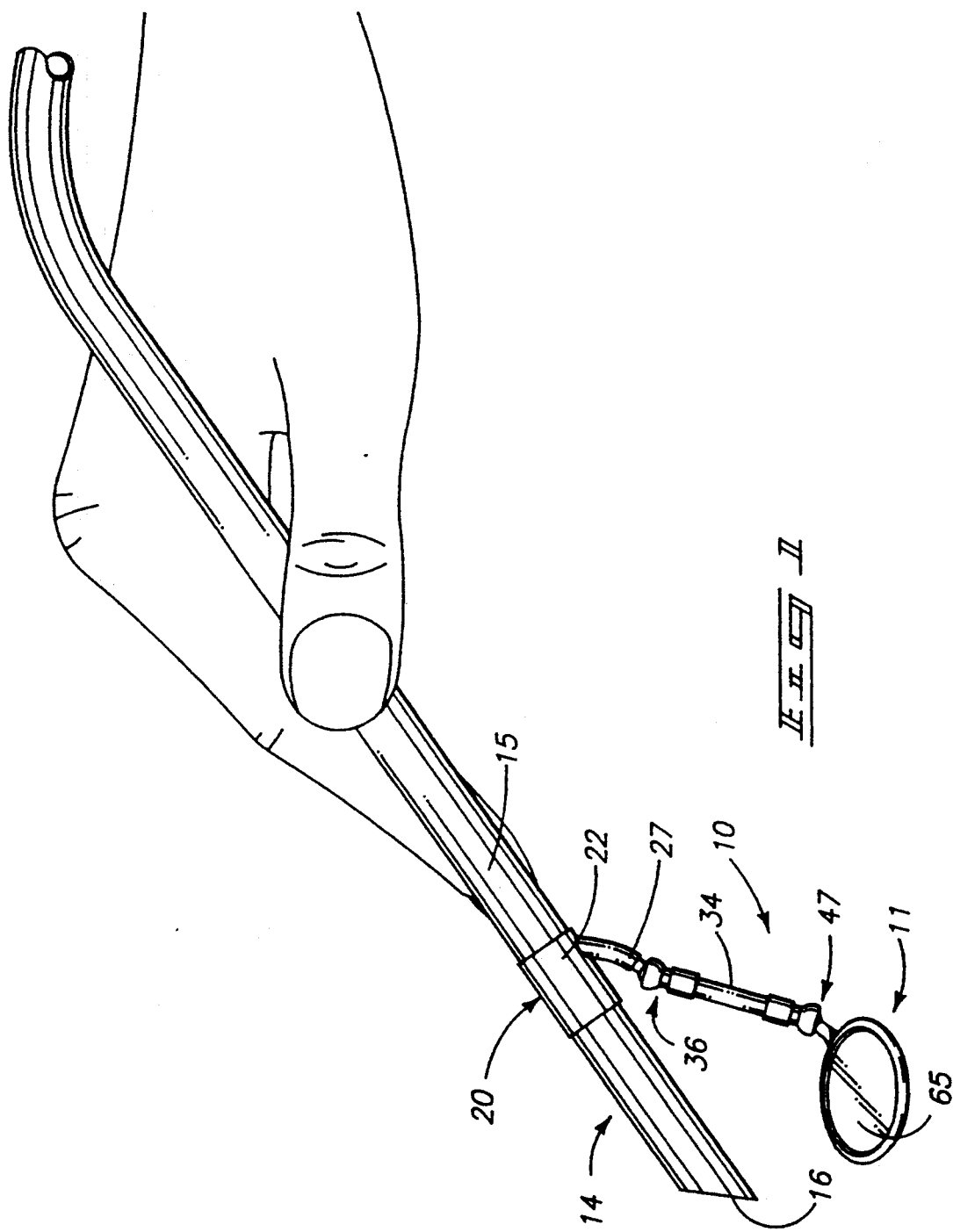

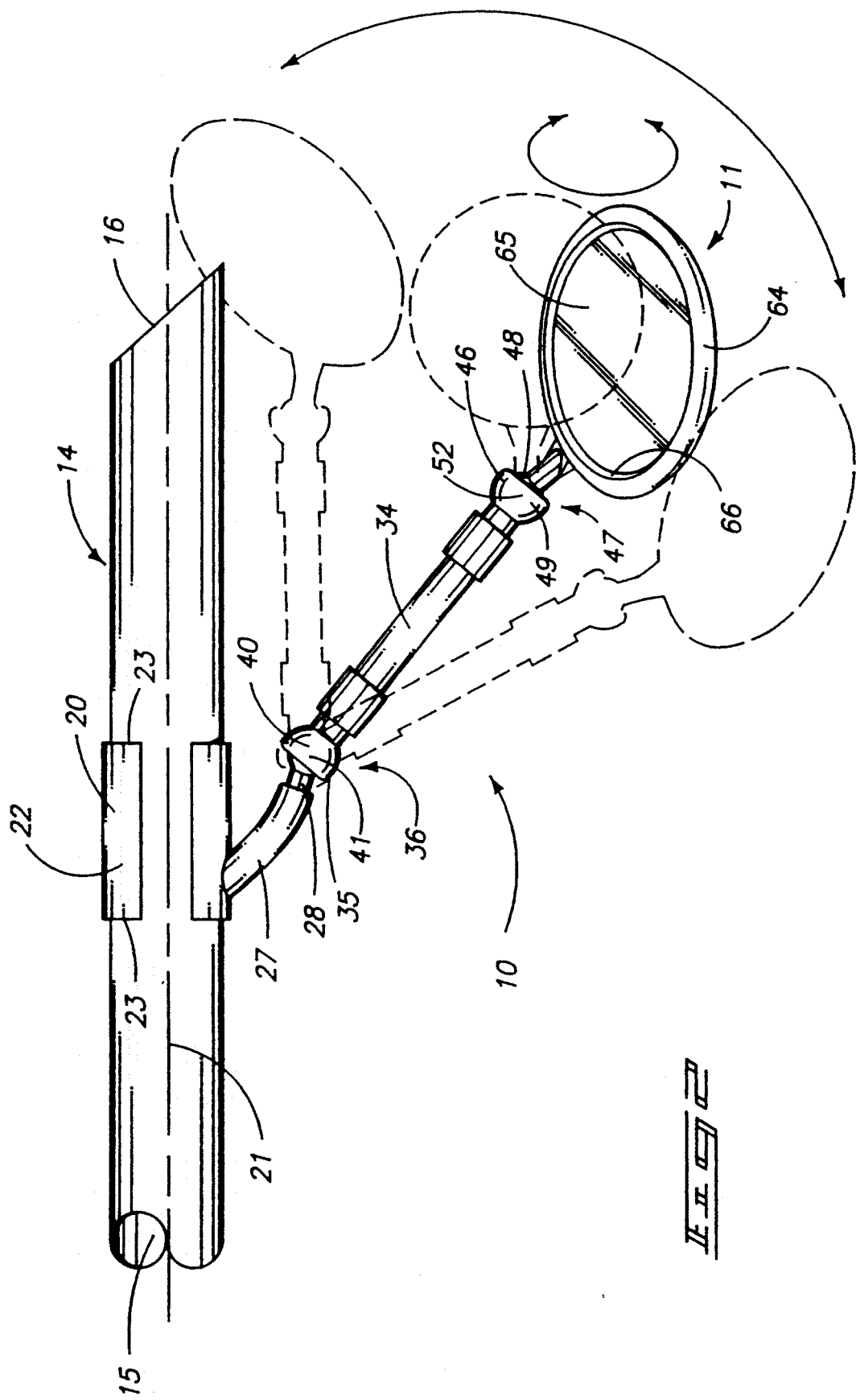

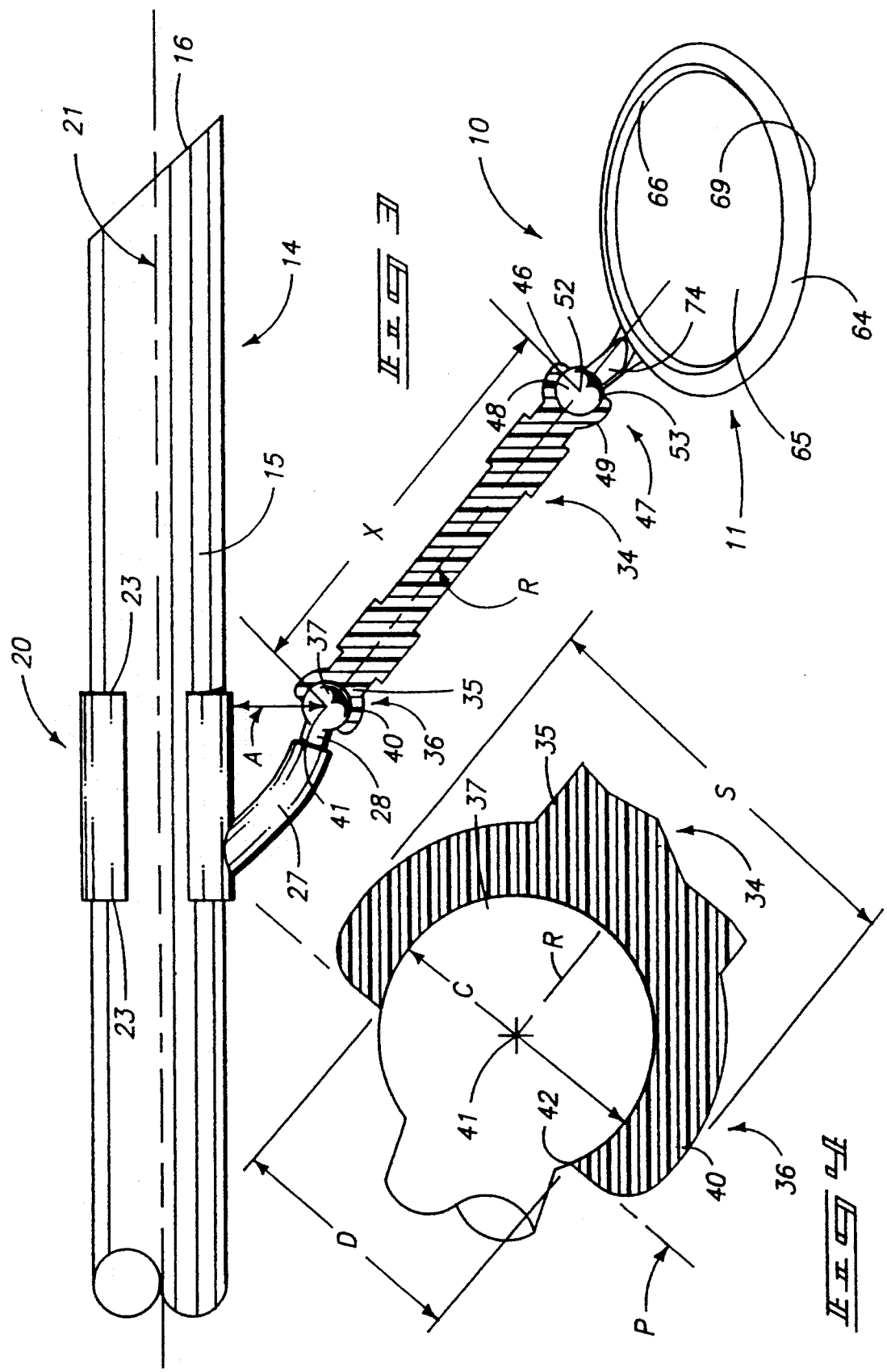

ARTICULATED MIRROR ATTACHMENT FOR DENTAL SUCTION TIPS

TECHNICAL FIELD

The present invention relates to dental mirrors and dental suction tips, particularly to a dental mirror that is adapted to be mounted to a dental suction tip and for angular adjustment thereon.

BACKGROUND OF THE INVENTION

It is difficult for dentists, and particularly difficult for dental students, to perform dental procedures on the upper arch of the patient's mouth while operating unassisted. This is due to the orientation of the upper arch and the normal position of the dentist relative to the patient's head. The direct view of the arch is obstructed unless the practioner or patient is positioned in an awkward, uncomfortable position to afford a direct view of the concerned area.

As a solution to this problem, dental mirrors have been developed to provide a view of the area for treatment, while dentist and patient are oriented in comfortable working positions. However, such mirrors present difficulties in use.

A hand must be used to hold the mirror while the other hand is used to support the instrument in current use to perform the desired procedure. While this arrangement would normally be acceptable, there is often a need to provide suction in the area. A third hand then becomes necessary (usually from an assistant) to direct the suction tip in the patient's mouth. This is the standard operating procedure in functioning dental offices. However, dental schools and small offices often do not have the personnel available to assist in such situations. Furthermore, it is somewhat difficult for the assistant to anticipate the need and direction for the suction tip during the various procedures. It therefore becomes desirable to provide means by which the practitioner alone may simultaneously control the tool for performing the dental procedure, the suction tip and a mirror, simultaneously.

The problem of supporting a mirror for dental purposes has been recognized to a limited degree. For example, U.S. Pat. Nos. 1,079,414 to Jirka, 159,836 to Osborn, and 4,354,835 to Lewis all disclose clamp mounted mirrors. These mirrors are connected to pivoted links which, in turn, are connected to a clamp that is provided to be secured to a rubber dam clamp on a tooth. A tooth or a rubber dam is entirely separate from any suction device. Thus, the entire mirror and support structure must be positioned within the patient's mouth. While this might be serviceable for certain procedures, it is undesirable for others where a larger field is required and where the mirror must be periodically removed and replaced, or when the tooth to be worked on is obstructed by the rubber dam clamp holding the pivoted mirror.

The above problems are also recognized to a limited degree in U.S. Pat. Nos. 3,777,756; 3,928,916; 2,861,342; 2,436,040; 1,905,633; 2,862,299; 2,393,319; and 838,648. The '756 patent, titled "Saliva Ejector", for example, discloses a suction pipe with a strainer end having a mirror (wing) attached thereto. The mirror is not adjustable, other than about the axis of the suction end, and may not be selectively positioned axially along the length of the suction tube, as the strainer end includes a closed end. Thus, the mirror finds only limited use. An integrated suction tip and mirror are also shown in U.S. Pat. Nos. 3,928,926; 2,861,342, and 2,436,040. These apparatus combine the mirror and suction tip or related appliance.

Of the above references, none provides an adequate solution to the problem typically encountered when a dental tool, suction device and mirror are all to be used in a confined area of a patient's mouth simultaneously. Nor do these arrangements provide optimal adjustment capabilities for the mirror to be positioned in a useful position, yet clear of the area being worked upon, all the while being in a desired position with respect to the dental suction tip.

BRIEF DESCRIPTION OF THE DRAWINGS

A preferred embodiment of the invention is described below with reference to the accompanying drawings, which are briefly described below.

FIG. 1 is a side elevation view of the present attachment shown in conjunction with a hand-held dental suction tip (shut-off valve and hose not shown for simplicity);

FIG. 2 is an enlarged view of the present attachment with a fragment of a suction tip shown, and with various positions of the mirror shown by dashed lines;

FIG. 3 is a view similar to FIG. 2 only with portions of the present attachment shown in section view with dimensions thereon; and FIG. 4 is an enlarged fragmentary sectional view of a ball joint means.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

An articulated mirror attachment is generally shown in drawings at 10 for attachment and adjustably mounting a mirror 11 to a conventional dental suction tip 14. The suction tip 14 is shown in FIG. 1, typically formed as a cylindrical tube 15, usually of plastic or other disposable material extending to a beveled open end 16.

The tube is releasably connected to a suction line and is meant to be hand held as shown in FIG. 1 for the purpose of removing air/water spray and debris from a patient's mouth during certain dental procedures. The present attachment 10 is provided to be releasably and adjustably mounted to the tip 14 so the practitioner is required to use only one hand to perform suctioning operations and, at the same time, have a clear reflected view of the site.

The preferred articulated mirror attachment 10 is releasably mountable to the dental suction tip 14 by way of a dental suction tip mounting collar 20. The collar 20 is formed about a central longitudinal dental suction tip axis 21 (FIGS. 2, 3). Axis 21, when the attachment is mounted to the suction tip 14, is coincidental or coaxial with the axis of the tip.

The collar 20 is advantageously formed as a tubular spring clip 22 split longitudinally, parallel to the tip axis. The collar is expandable to be received over the suction tip substantially as shown. The collar has sufficient resiliency to assure a firm grip on the suction tip while permitting adjustment along the length of the suction tip and about the central axis 21. The collar 20 extends axially between opposed ends 23.

A stud shaft 27 projects at an angle from the collar 20. A base end of the stud shaft 27 is situated near one of the collar ends 23. It extends outwardly and toward the opposite collar end. The stud shaft terminates at a stud shaft end 28 which includes a first ball joint means 36.

Outward of the stud shaft 27 is an extension arm 34. Arm 34 includes an end 35 which is mounted to the stud shaft by way of the first ball joint means 36. The joint means 36 includes a socket 40 on the extension arm 34 for releasably and pivotably receiving the ball member 37 (FIG. 3). The extension arm will pivot about a first center point 41 which is coincidental with the centers of the socket and ball.

The socket 40 has an outward diameter S (FIG. 4) that, in a preferred form, is less than the distance A (FIG. 3) between the collar 20 and first ball joint 36. This spacing relationship and the angular orientation of the stud shaft 27 assures that the arm 34 can be pivoted relatively freely to a desired position in the vicinity of the suction tip 14. FIG. 2 exemplifies several positions.

The first socket 40 on the extension arm 34 includes a circular end opening 42 (FIG. 4) therein that is of slightly smaller diameter than the first ball diameter. In fact, it is desirable to provide for a press fit between the ball and socket so the ball will snap into engagement with the socket, yet so both will allow relatively free positioning of the arm about the first center point 41. To this end, a press fit tolerance between the ball and socket is desirable. In practice, a diameter differential between the ball and socket of $-0.001$ inches has been found advantageous. This "tolerance" between ball and socket results in a stiff frictional relationship whereby the elements will pivot relative to one another, but will normally hold their position during use.

The extension arm 34 extends from end 35 to an opposite end 46 which includes a second ball joint means 47. The second ball joint means is provided for pivotably mounting the mirror assembly 11 to the extension arm for pivotal motion thereon about a second center point 52.

The second ball joint means may be substantially identical to the first ball joint means. It includes a ball member 48 on the mirror assembly 11 and a socket 49 on the extension arm 34. The socket 49 includes a circular opening therein that is smaller in size than the second ball diameter. The tolerance mentioned above may also be utilized for this ball and socket joint.

The circular openings 42, 53 are formed on parallel planes P (FIG. 4) that are substantially perpendicular to the long axis R of the extension arm 34. The orientation of these openings with respect to the axis affects the angular limits about which the arm and mirror will pivot on points 41 and 52.

The length dimension of the extension arm between ball centers is preferably within a range between ¾ and 1.5 inches. Within this range, approximately 1.25 inches between centers 41, 52 is preferred.

The mirror assembly 11 includes a planar, preferably circular reflective plate 65 (FIG. 3). The plate 65 leads into a peripheral marginal edge 64 of the mirror assembly. The edge 64 is a portion of a backing member 69 in which the marginal edge portion is crimped over to form a peripheral plate overlapping edge 66 to retain the mirror in position.

A stub shaft 74 projects outwardly from the marginal edge 70 at an angle (FIGS. 2, 3) from the plane of the reflective planar mirror surface. Stub shaft 74 mounts the second ball member 48. The stub shaft extends from the marginal edge of the assembly to free the under or back side of the mirror, thereby permitting the mirror to be positioned in confined areas with respect to the tip of the suction tip and the adjacent tissues within the patient's mouth.

The entire structure of the present articulated mirror attachment 10, with the exception of the mirror plate 65, may be constructed advantageously from an autoclavable thermoplastic material. An acceptable form of such material is polyethersulfone sold under the tradename "ULTRASON E" ™ by BASF Company of Parsippany, N.J. This material may be injection molded in the configuration and tolerances preferred for the present invention.

In operation, the present attachment may be easily attached to an existing suction tip 14. This is accomplished simply by sliding the spring clip axially over the open end of the suction tip, or by simply pressing the clip laterally over the diameter of the tip. The split clip will separate and spring back to frictionally engage a clamp against the suction tube.

Frictional engagement by the collar 20 permits the attachment to remain in whatever position is selected along the length of the tube or about a central longitudinal axis thereof. This represents one adjustment capability for the device.

The adjustment is usually made such that the length of the attachment from the clip to the mirror is approximately equal to or slightly greater than the distance between the clip and the open end of the suction tube. This relationship is best shown in FIG. 1 of the drawings. With the attachment mounted to the tube 14, other adjustments may be made periodically to set the mirror 11 in position for the most advantageous viewing position.

This is done simply by grasping the mirror 11 and moving it into the desired position. The two ball joints will facilitate nearly any pivotal movement whatsoever while the axial position may be adjusted simply by sliding the clip up or down the length of the tube. Thus, the user is capable of setting the mirror at any desired angle.

The mirror will remain at the selected angle until adjusted otherwise. Thus, the user is able to use a single hand, as shown in FIG. 1, both for positioning the mirror and for positioning the suction tip. The remaining hand is thereby free to operate whatever tool is to be used during the desired procedure.

The attachment may be removed from the dental suction tip after use. It may then be dismantled and autoclaved for future use. The device can then be snapped back together simply by snapping the ball ends over the sockets and thereby completing the assembled attachment and readying it for subsequent use.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. An articulated mirror attachment for dental suction tips, comprising:
   a dental suction tip mounting collar formed about a dental suction tip axis and adapted to be slidably mounted to a dental suction tip for selective sliding movement thereon and rotation about said dental suction tip axis;

said collar having substantially cylindrical inner and outer surfaces and opposed ends;

a stud having a stud end and having a stud shaft projecting from said outer cylindrical surface of the dental suction tip mounting collar near one of said opposed ends to so that said stud shaft is angled in relation to said dental suction tip axis, such that the stud end is oriented toward the other opposed collar end;

a mirror;

an extension arm having opposed ends;

first ball joint means mounting one end of the extension arm to the stud end, for permitting pivotal movement of the extension arm and collar relative to one another through an arc about a first center point; and second ball joint means mounting the remaining end of the extension arm to the mirror, for permitting pivotal movement of the extension arm and mirror relative to one another about a second center point.

2. An articulated mirror attachment for dental suction tips, as claimed by claim 1, wherein the first and second ball joint means include ball members mounted on the stud and mirror, and sockets mounted to the extension arm, releasably receiving the ball members.

3. An articulated mirror attachment for dental suction tips, as claimed by claim 1, wherein the first and second ball joint means include ball members mounted on the stud and mirror, and sockets mounted to the extension arm, releasably receiving the ball members, said sockets including circular openings therein smaller than diameters of the ball members to provide a releasable snap fit between the ball members and the sockets on the extension arm.

4. An articulated mirror attachment for dental suction tips, as claimed by claim 1, wherein the extension arm includes a length dimension between its opposed ends between approximately 0.75 inches and 1.5 inches.

5. An articulated mirror attachment for dental suction tips, as claimed by claim 1, wherein the mirror includes a peripheral marginal edge and wherein the second ball means includes a ball part and a socket part, with one of said parts being mounted to the mirror along the marginal edge thereof.

6. An articulated mirror attachment for dental suction tips, as claimed by claim 1, wherein the mirror includes a peripheral marginal edge and wherein the second ball means includes a ball part on the extension arm and a socket part on the mirror along the marginal edge thereof.

7. An articulated mirror attachment for dental suction tips, as claimed by claim 1, wherein the first ball joint means includes a ball part on the stud at the stud end, and a socket part on one of the opposed ends of the extension arm receiving the ball part, the socket part having an external diameter; and wherein the stud end is spaced away from the collar by a distance greater than the external diameter of the socket part.

8. An articulated mirror attachment for dental suction tips, as claimed by claim 1, wherein the first and second ball joint means are comprised of ball parts and socket parts, and wherein the socket parts are formed at the opposed ends of the extension arm and include ball receiving openings therein formed on substantially parallel planes, and wherein said substantially parallel planes are substantially perpendicular to the extension arm axis.

9. An articulated mirror attachment for dental suction tips, as claimed by claim 1, wherein the mirror includes a marginal edge portion and a stub shaft extending from the marginal edge portion to a stub shaft end and wherein the second ball joint means is situated at the stub shaft end.

10. An articulated mirror attachment for dental suction tips, as claimed by claim 1, wherein the extension arm includes a length dimension of approximately 1.25 inches between ends thereof.

11. An articulated mirror attachment for dental suction tips, as claimed by claim 1, wherein the mirror includes a planar reflecting surface and includes a stub shaft extending from a marginal edge portion thereof, at an angle to the planar reflecting surface.

12. An articulated mirror attachment for dental suction tips, as claimed by claim 1, wherein the collar is a substantially tubular spring clip, split longitudinally, parallel to the suction tip axis.

13. An articulated mirror attachment for dental suction tips, as claimed by claim 1, wherein the mirror is comprised of:

a planar reflective plate having a peripheral edge;

a backing member with a marginal edge crimped over the peripheral edge of the reflective plate; and wherein the second ball joint means is comprised of a ball member on the marginal edge of the backing member and a socket member located between the marginal edge of the backing member and one end of the extension arm.

14. An articulated mirror attachment for dental suction tips, as claimed by claim 1, wherein the first and second ball joint means include ball members including ball diameters, and sockets, releasably receiving the ball members with internal socket diameters and wherein the internal socket diameters are approximately 0.001 inches less than the corresponding ball diameters to provide a press fit for said ball members, and thereby produce a stiff ball and socket joint that will hold its position.

* * * * *